United States Patent
Kaneko et al.

[11] Patent Number: 6,099,654
[45] Date of Patent: Aug. 8, 2000

[54] PROCESS FOR RECOVERING BETAINE

[75] Inventors: Kikuzo Kaneko; Takayuki Masuda; Fumihiko Matsuda; Kohei Sato; Kouji Tanikawa, all of Tokyo, Japan

[73] Assignee: Organo Corporation, Tokyo, Japan

[21] Appl. No.: 09/367,690
[22] PCT Filed: Dec. 24, 1998
[86] PCT No.: PCT/JP98/05843
§ 371 Date: Aug. 19, 1999
§ 102(e) Date: Aug. 19, 1999
[87] PCT Pub. No.: WO99/33784
PCT Pub. Date: Jul. 8, 1999

[30] Foreign Application Priority Data

Dec. 25, 1997 [JP] Japan .................. 9-366255

[51] Int. Cl.$^7$ .................. C07B 63/00; C07C 229/12
[52] U.S. Cl. .................. 127/46.2; 127/46.3
[58] Field of Search .................. 127/46.2, 46.3; 562/554

[56] References Cited

U.S. PATENT DOCUMENTS 3,975,205  8/1976  Munir et al. .
4,359,430  11/1982 Heikkila et al. .

FOREIGN PATENT DOCUMENTS 34094    12/1964  Germany .
81 02420  9/1981  WIPO .

OTHER PUBLICATIONS

Database WPI, Section Ch, Week 9420, Derwent Publications Ltd., London, G.B.; Class D13, An 94–163887, XP002098451, & JP 06 107611 (Hokuren Nogyo Kyodo Kumiai), Apr. 19, 1994.

Database WPI, Section Ch, Week 8923, Derwent Publications Ltd., London, G.B.; Class D17, An 89–168678, XP002098453 & JP 01 109000 A (Hokuren Nogyo Kyodo Kumiai—Mitsubishi Kasei Techno), Apr. 26, 1989.

Database WPI, Section Ch, Week 9630, Derwent Publications Ltd., London, G.B.; Class D17, An 96–298740, XP002098454, & RU 2 048 847 (Mitchenko T E, Nov. 27, 1995.

Database WPI, Section Ch, Week 7620, Derwent Publications Ltd., London, G.B.; Class B02, AN 76–37196X, XP002098455, & JP 51 039625, (Nippon Beet Sugar KK), Apr. 2, 1976.

Primary Examiner—Gary Geist
Assistant Examiner—Leigh C. Maier
Attorney, Agent, or Firm—Norris, McLaughlin & Marcus, P.A.

[57] ABSTRACT

A starting solution material in the form of waste produced in the course of separation and recovery of sucrose from sugar beet extract or sugar beet molasses with a 2-component separation simulated moving bed chromatographic separator (using a strongly acidic cation exchange resin in a salt form as chromatographic packing) or its concentrate is used to separate therefrom a crude betaine fraction with a 2-component separation simulated moving bed chromatographic separator using as chromatographic packing a strongly acidic cation exchange resin in an ionic form equilibrated with that of the starting solution material. The crude betaine fraction or its concentrate is used to separate therefrom a betaine fraction with a 2-component separation simulated moving bed chromatographic separator using as chromatographic packing a strongly acidic cation exchange resin having at least 10% (based on the ion exchange capacity) of the ionic form thereof changed to the Ca form. The betaine fraction may be concentrated and subjected to crystallization, whereby high-purity betaine can be obtained.

4 Claims, 5 Drawing Sheets

FIG. 2
[BETAINE RECOVERY PROCESS AS CONVENTIONAL METHOD (1)]
SUGAR BEET MOLASSES
CHROMATOGRAPHIC SEPARATION (BATCH, CATION EXCHANGE RESIN IN ALKALI METAL ION FORM)
      
① CRUDE BETAINE SOLUTION   ② SUCROSE SOLUTION   ③ OTHERS (DISPOSAL)
(This may be returned to first chromatographic separation when low in sucrose concentration.)
CONCENTRATION
CRYSTALLIZATION

FIG. 3

[BETAINE RECOVERY PROCESS AS CONVENTIONAL METHOD (2)]

SUGAR BEET MOLASSES

↓

FIRST CHROMATOGRAPHIC SEPARATION (BATCH, CATION EXCHANGE RESIN IN
                                    ALKALI METAL ION FORM, IN Na FORM IN
                                    EXAMPLE)

↓                        ↓                      ↓

① CRUDE BETAINE SOLUTION     ② SUCROSE SOLUTION     ③ OTHERS (DISPOSAL)

( This may be returned to
                                       first chromatographic
                                       separation when low in
                                       sucrose concentration. )

↓

CONCENTRATION

↓

SECOND CHROMATOGRAPHIC SEPARATION (BATCH+RECIRCULATION, CATION
                                          EXCHANGE RESIN IN ALKALI METAL ION
                                          FORM, IN Na FORM IN EXAMPLE)

↓

CRYSTALLIZATION

↓                        ↓                      ↓

① HIGH-PURITY BETAINE      ② OTHERS (DISPOSAL)     ③ LOW-PURITY BETAINE
   SOLUTION                                                     SOLUTION ( This may be returned to
                                                                    second chromatographic
↓                                                             separation. )

CONCENTRATION

↓

CRYSTALLIZATION

FIG. 4

[BETAINE RECOVERY PROCESS AS CONVENTIONAL METHOD (3)]

MOLASSES IN BEET SUGAR INDUSTRY FOR SUGAR
PRODUCTION WITH ION EXCHANGE RESIN

↓

CHROMATOGRAPHIC SEPARATION (MULTI-COMPONENT SEPARATION SIMULATED
MOVING BED CHROMATOGRAPHIC SEPARATOR)

| ↓ | ↓ | ↓ | ↓ |
|---|---|---|---|
| ① BETAINE SOLUTION | ② SUCROSE SOLUTION | ③ RAFFINOSE SOLUTION | ④ MONOSACCHARIDES SOLUTION |

↓

CONCENTRATION

↓

CRYSTALLIZATION

PROCESS FOR RECOVERING BETAINE

TECHNICAL FIELD

The present invention relates to a process for recovering betaine, and more particularly to a process for recovering high-purity betaine from waste in the beet sugar industry. Herein, the term "waste in the beet sugar industry" indicates waste produced in the course of separation and recovery of sucrose from sugar beet extract or sugar beet molasses with a 2-component separation simulated moving bed chromatographic separator using a strongly acidic cation exchange resin in a salt form as chromatographic packing. The term "from sugar beet extract" as used in the present invention is intended to mean "starting from extract" obtained through the extraction step during the course of refining and recovery of sucrose from sugar beet according to a variety of process comprising a series of steps of cutting, extraction, filtration, softening, chromatographic separation, etc. Thus, a solution to be subjected to the above-mentioned step of chromatographic separation is of course a solution obtained after various necessary steps taken beforehand. In this respect, the term "from sugar beet molasses" is intended to have the same meaning as described above. Incidentally, betaine is a substance occurring in roots, grains and stems of various plants and contained in a comparatively large amount in sugar beet in particular, and is a useful substance which is used as animal feed, a starting material of pharmaceutical preparations, a staring material of cosmetic preparations, etc.

BACKGROUND ART

The following 3 methods are known as examples of the conventional betaine recovery methods.

A method (1) is one as disclosed in claim 1 of Japanese Patent Publication No. 50,895/1990 wherein diluted molasses having a solids content of 20 to 50 wt. % is batchwise passed through a chromatographic column packed with a strongly acidic cation exchange resin (crosslinked with 2 to 12 wt. % of divinylbenzene) in the form of an alkaline metal salt at a resin bed height of 2.5 to 10 m to recover a betaine fraction (see the flow chart of FIG. 2 for further particulars).

A method (2) is one as disclosed in claims 2 and 3 of Japanese Patent Publication No. 50,895/1990 wherein a crude betaine solution (betaine fraction) obtained according to the foregoing method of claim 1 is batchwise passed through the foregoing chromatographic column (claim 2) to recover a higher-purity betaine fraction while a lower-purity betaine fraction obtained at this time is also separately recovered and recirculated (claim 3) to recover betaine in this fraction as well (see the flow chart of FIG. 3 for further particulars).

A method (3) is one as disclosed in Proceedings of the Research Society of Japan Sugar Refineries' Technologists, Vol. 41 pp. 29–36 (1993) wherein molasses produced in a beet sugar factory where a method of manufacturing sucrose by ion exchange refining is adopted is separated with a multi-component separation simulated moving bed chromatographic separator to recover betaine (see the flow chart of FIG. 4 for further particulars).

The foregoing conventional methods of recovering betaine are all used for a solution having a comparatively low salts concentration with no consideration given to the fact that the ionic form of the cation exchange resin is changed by salts.

However, waste produced in the course of separation and recovery of sucrose from sugar beet extract or sugar beet molasses with a 2-component separation simulated moving bed chromatographic separator using a strongly acidic cation exchange resin in a salt form as chromatographic packing contains 5–20 wt. % sucrose, 40–75 wt. % salts, 5–20 wt. % betaine, 1–10 wt. % monosaccharides and 0.5–5 wt. % unknown substances based on solids (i.e., based on dry solids). Thus, when this waste is concentrated to a solids content of about 50% (weight/solution weight), the salts concentration of the resulting concentrate becomes several in normality.

When such salts-rich waste derived from a plant (e.g., beet) or its concentrate is passed as a starting solution material through a chromatographic column packed with a cation exchange resin, 40 to 80% of the ionic form of the cation exchange resin becomes the K form because of a large amount of potassium ions existing in the starting solution material, thus leading to poor separation of betaine from monosaccharides such as glucose, fructose and inositol, and other unknown substances. Accordingly, there inevitably arises a problem that high-purity betaine cannot be obtained by chromatographic separation wherein a cation exchange resin is used as chromatographic packing.

For example, the partition coefficients of components in the starting solution material by a strongly acidic cation exchange resin Amberlite (registered trademark) CR-1320 for chromatographic separation (manufactured by Rohm and Haas Company) in an ionic form equilibrated with that of residual waste produced after recovery of sucrose from a certain sugar beet molasses are 0.19 for salts, 0.24 for trisaccharides, 0.30 for sucrose, 0.39 for unidentified disaccharides, 0.45 for glucose, 0.47 for betaine, 0.51 for a fructose+inositol mixture, 0.54 for unidentified monosaccharides, and 0.59 for unknown substances (impurities believed to be nucleic acids, etc.) other than saccharides in the eluting (outflowing) order. Thus, it has been understood that the simulated moving bed procedure of separation of 2 components can separate betaine from salts, trisaccharides, sucrose, and unidentified disaccharides, but involves a difficulty in separating betaine from monosaccharides and unknown substances. Incidentally, the ionic form composition (based on ion exchange capacity) of the cation exchange resin in this case has turned out to consist of 26% Na form, 73% K form and 1% Ca form. Poor separation is of course inferable from these values of partition coefficients. This was substantiated from the fact that the betaine purity was only at most about 82% based on solids (in terms of areal percentage in high-performance liquid chromatography using a sodium-form ion exchange column and a differential refractometer) even with a simulated moving bed chromatographic separator best in separating efficiency in Comparative Example 1 described later.

Accordingly, an object of the present invention is to provide a process for recovering high-purity betaine from either waste having a high salts concentration in the solids-based composition thereof and produced in the chromatographic separation procedure in the beet sugar industry or its concentrate.

DISCLOSURE OF THE INVENTION

As a result of extensive investigations on the foregoing prior art technologies, the inventors of the present invention have solved the problems of the conventional betaine recovery methods to complete the present invention.

In order to attain the foregoing object, the betaine recovery process of the present invention is characterized in that a demineralization chromatographic separation operation of removing most of salts contained in high concentration in the foregoing waste or concentrate is performed using a strongly acidic cation exchange resin as chromatographic packing in Step 1, and that another chromatographic separation operation is performed using a strongly acidic cation exchange resin changed, or converted, by at least 10% (based on the ion exchange capacity) in ionic form to the Ca form in Step 2.

More specifically, the present invention provides a process for recovering betaine from a starting solution material in the form of waste produced in the course of separation and recovery of sucrose from sugar beet extract or sugar beet molasses with a 2-component separation simulated moving bed chromatographic separator using a strongly acidic cation exchange resin in a salt form as chromatographic packing or its concentrate; characterized by comprising Step 1 of separating a demineralized crude betaine fraction from the starting solution material with a 2-component separation simulated moving bed chromatographic separator using as chromatographic packing a strongly acidic cation exchange resin in an ionic form equilibrated with that of the starting solution material, and Step 2 of separating and recovering a betaine fraction from the crude betaine fraction or its concentrate with a 2-component separation simulated moving bed chromatographic separator using as chromatographic packing a strongly acidic cation exchange resin having at least 10% (based on the ion exchange capacity) of the ionic form thereof changed to the Ca form.

Replacement with ion exchange of the demineralization chromatographic separation operation in Step 1 of the process of the present invention is not suitable because the starting solution material has a high salts concentration of at least about 1 in terms of normality or a high salts content based on the solids thereof to decrease the throughput.

The 2-component separation simulated moving bed chromatographic separator to be used in the present invention is equipment for separating components contained in the starting solution material into 2 fractions, an example of which is a separator constructed in such a way that a starting solution material feed inlet, an eluent feed inlet, an extract withdrawal outlet and a raffinate withdrawal outlet are displaced in the downstream direction at predetermined time intervals. Use can be made either of a representative 2-component separation simulated moving bed chromatographic separator as disclosed in Japanese Patent Publication No. 15,681/1967, or of various simulated moving bed chromatographic separators altered therefrom, examples of which include those disclosed in Japanese Patent Laid-Open Nos. 49,159/1990, 141,311/1996, and 367,701/1992. Thus, the term "2-component separation simulated moving bed chromatographic separator" as used in the present invention is intended to encompass these various separators.

The ionic form of a gel type strongly acidic cation exchange resin that may be used as chromatographic packing at the beginning of operation in Step 1 may as well become a monovalent ion form to such an extent as not substantially to form insoluble salts with anions in the starting solution material when the cations of the resin are migrated into the liquid phase by ion exchange until that ionic form becomes an ionic form equilibrated with that of the starting solution material. In this sense, it will suffice that at least 95% (based on ion exchange capacity) of the ionic form of the strongly acidic cation exchange resin is composed of monovalent ion forms such as the Na form, the K form and the ammonium form. The ionic form of the cation exchange resin reaches an ionic form composition equilibrated with various ions contained in the starting solution material in keeping with the progress of operation. The ionic form equilibrated with that of the starting solution material will suffice for the purpose of demineralization. Incidentally, since the starting solution material is waste produced in the course of separation and recovery of sucrose from sugar beet extract or sugar beet molasses with a 2-component separation simulated moving bed chromatographic separator using a strongly acidic cation exchange resin in a salt form as chromatographic packing or its concentrate and hence is usually softened before the operation of separation and recovery of sucrose with the chromatographic separator, almost all ions contained in the starting solution material are monovalent ions.

When part (at least 10%) or the whole (based on ion exchange capacity) of the ionic form of the strongly acidic cation exchange resin is changed to the Ca form before Step 2, a difference between the partition coefficient of betaine and those of impurities in respect of recovering betaine, such as monosaccharides and unknown substances, is widened to enable efficient separation therebetween. For example, the partition coefficient in the case of Amberlite CR-1320 in the Ca form is 0.46 for glucose, 0.50 for the fructose+inositol mixture, 0.70 for unidentified monosaccharides, 0.94 for unknown substances other than saccharides, and 1.19 for betaine, thus indicating easy separation of betaine from monosaccharide and unknown substances.

Where the amount of unknown substances is so small in the starting solution material that they may be contained in a betaine fraction, it will suffice that betaine can be separated only from monosaccharides. In this case, therefore, the whole ionic form of the strongly acidic cation exchange resin is not necessarily changed to the Ca from, but only 10% thereof based on the ion exchange capacity may sometimes be changed to Ca form. Accordingly, the ionic form of the strongly acidic cation exchange resin to be used in Step 2 is changed to the Ca form in an amount of at least 10%, preferably at least 30%, further preferably at least 50%, based on the ion exchange capacity. However, this does not necessarily mean that the ionic form of the strongly acidic cation exchange resin in every one of the packing bed units of the simulated moving bed chromatographic separator should be changed to the Ca form in an amount of at least 10% based on the ion exchange capacity, but means that at least part of the ionic form of the strongly acidic cation exchange resin in at least one packing bed unit is changed to the Ca from in such a way that the ionic form as a whole of the total strongly acidic cation exchange resin in all the packing bed units should be changed to the Ca form in an amount of at least 10% based on the ion exchange capacity.

There also is a case where part of the strongly acidic cation exchange resin is left intact in a monovalent ion form in an aspect of suitably adjusting separation of betaine from unknown substances. Incidentally, since a starting solution such as a crude betaine solution or its concentrate to be subjected to Step 2 is depleted of most of salts, the Ca form as a bivalent ion form is not easily changed to a monovalent ion form during Step 2, whereby a good separation performance can be maintained during the desired period of operation.

In the beet sugar industry, factories are generally run intensively for 3 to 4 months in winter, for example, in Japan. Thus, it is favorable in an aspect of saving the equipment cost that a crude betaine fraction obtained after the completion of demineralization operation with a simulated moving bed chromatographic separator in Step 1 be concentrated and stored once, followed by effecting separation in Step 2 with the same simulated moving bed chromatographic separator in a season shifted from the winter season during which the factories are intensively run. This can be satisfied when the ionic form of the cation exchange resin is adjusted each time in such a way that at least 95% (based on ion exchange capacity) of the ionic form of the cation exchange resin is changed to a monovalent alkali ion form such as the Na form, the K form and/or the ammonium form before start of Step 1 while at least 10% thereof based on the ion exchange capacity is changed to the Ca form before start of Step 2. Needless to say, however, the process of the present invention may be carried out using separate simulated moving bed chromatographic separators for respectively taking Step 1 and Step 2.

A generic and simple description will now be made of a representative example of 2-component separation simulated moving bed chromatographic separator that can be used in the process of the present invention. The separator comprises a system (loop) comprising a plurality of packing bed units linked in endless series and packed with solid sorbent (a strongly acidic cation exchange resin in a salt form as chromatographic packing in the present invention), a means for circulating internal fluid in one direction in the system, a starting material feed means for choosing any one of the packing bed units and feeding thereto a starting material (a starting solution material in the form of waste produced in the course of separation and recovery of sucrose from sugar beet extract or sugar beet molasses with a 2-component separation simulated moving bed chromatographic separator using a strongly acidic cation exchange resin in a salt form as chromatographic packing or its concentrate in Step 1, or a crude betaine fraction solution obtained through Step 1 or its concentrate in Step 2 in the present invention), an eluent feed means for choosing any other one of the packing bed units and feeding thereto eluent (eluent water in the present invention), a first fluid withdrawal means for choosing any one of the packing bed units and withdrawing therefrom raffinate (nonbetaine fraction solution in the present invention) out of the system, a second fluid withdrawal means for choosing any other one of the packing bed units and withdrawing therefrom extract (betaine fraction solution in the present invention) out of the system, and a switching control means for sequentially displacing the fluid feed positions and the fluid withdrawal positions in the downstream direction of fluid flow in the system while maintaining the relationship between the fluid feed positions and the fluid withdrawal positions in the system in addition to control of the fluid flow rate in the system.

A generic and simple description will now be made of an example of a 2-component separation simulated moving bed chromatographic process using this simulated moving bed chromatographic separator. The group of the packing bed units linked in endless series is regarded as being divided into first, second, third and fourth sections in the downstream direction of fluid flow when viewed from the eluent feed position. Eluent (eluent water in the present invention) is fed via a feed valve to circulating fluid at the inlet of a packing bed unit positioned foremost in the first section and extract [(crude) betaine fraction solution in the present invention] large in the amount of a sorbed component is withdrawn via a withdrawal valve from circulating fluid at the outlet of a packing bed unit positioned rearmost in the first section, while the starting material is fed via a feed valve to circulating fluid at the inlet of a packing bed unit positioned foremost in the third section and raffinate (nonbetaine fraction solution in the present invention) small in the amount of the sorbed component is withdrawn via a withdrawal valve from circulating fluid at the outlet of a packing bed unit positioned rearmost in the third section. The eluent feed position, the extract withdrawal position, the starting material feed position, and the raffinate withdrawal position are each operationally displaced one by one in the downstream direction in keeping with the movement of a zone wherein the component in the starting material is sorbed on sorbent.

BRIEF DESCRIPTION OF THE DRAWINGS

FIG. 2 is a flow chart for illustrating the outline of the operation procedure of carrying out an example of conventional method of recovering betaine;

FIG. 3 is a flow chart for illustrating the outline of the operation procedure of carrying out another example of conventional method of recovering betaine;

FIG. 4 is a flow chart for illustrating the outline of the operation procedure of carrying out still another example of conventional method of recovering betaine.

MODES FOR CARRYING OUT THE INVENTION

Modes for carrying out the present invention will now be described while referring to the accompanying drawings, but should not be construed as limiting the scope of the present invention unless they depart from the subject matter of the present invention.

Figure 1:
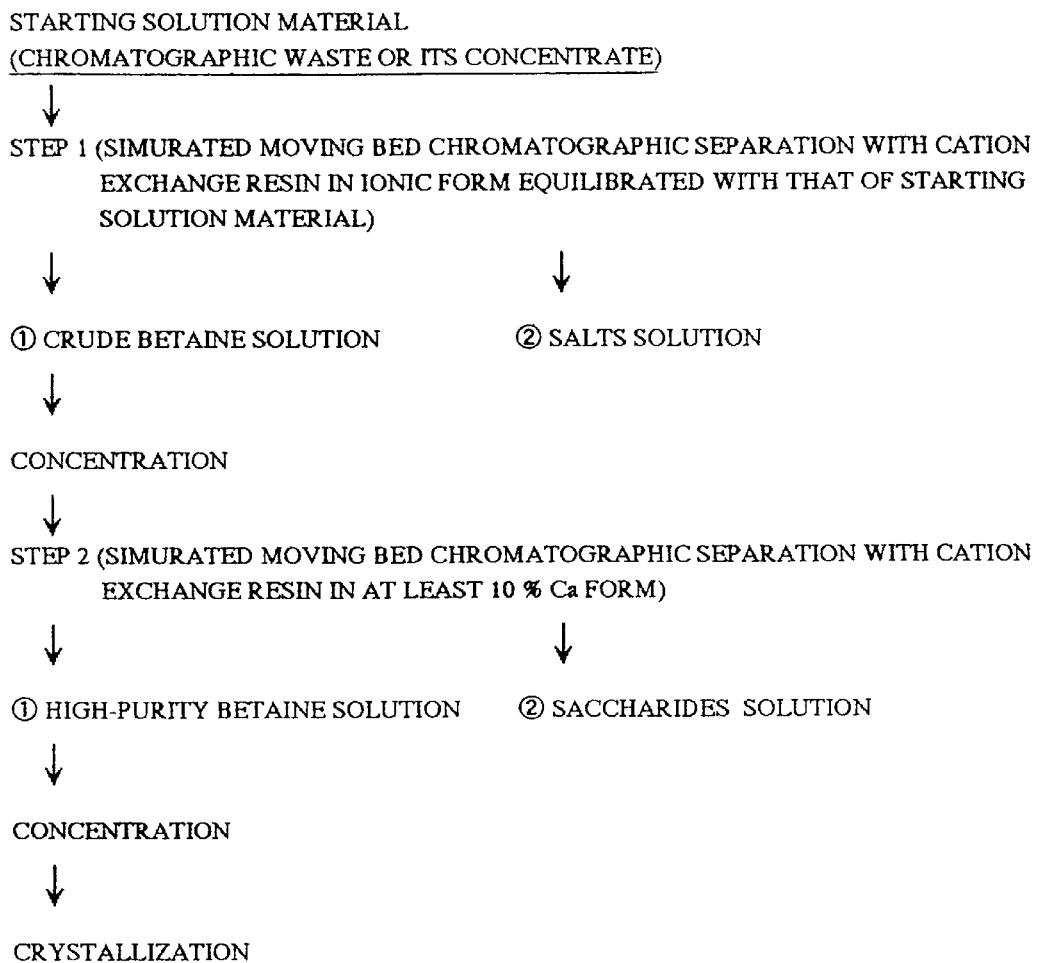
FIG. 1 is a flow chart for illustrating the outline of the operation procedure of carrying out the process of the present invention.

FIG. 1 is a flow chart for illustrating the outline of the operation procedure of carrying out the process of the present invention. In FIG. 1, the starting solution material refers to waste produced in the course of separation and recovery of sucrose from sugar beet extract or sugar beet molasses with a 2-component separation simulated moving bed chromatographic separator using a strongly acidic cation exchange resin in a salt form as chromatographic packing or its concentrate, which contains a large amount of salts. The starting solution material is first separated into a crude betaine solution (betaine fraction) depleted of most of salts and a salts solution (salts fraction, i.e., nonbetaine fraction) with a 2-component separation simulated moving bed chromatographic separator packed with a strongly acidic cation exchange resin equilibrated in ionic form with the starting solution material (Step 1). The crude betaine solution or its concentrate (preferably its concentrate) is then separated into a saccharides solution (saccharides fraction, i.e., nonbetaine fraction) enriched with saccharides and other impurities and a high-purity betaine solution (betaine fraction) with the simulated moving bed chromatographic separator packed with the strongly acidic cation exchange resin having part (at least 10% based on the ion exchange capacity) or the whole of the ionic form thereof changed to the Ca form as chromatographic packing (Step 2). In the present invention, the operating temperature at which the simulated moving bed chromatographic separator is run is preferably 60 to 90° C., most preferably around 80° C., in order to prevent growth of bacteria in the liquid inside the separator and keep the liquid at a low viscosity. Incidentally, the fractionated high-purity betaine solution is subsequently concentrated, and then subjected to a crystallization operation according to a customary method, if necessary, to obtain high-purity betaine crystals.

EXAMPLES

Figure 5:
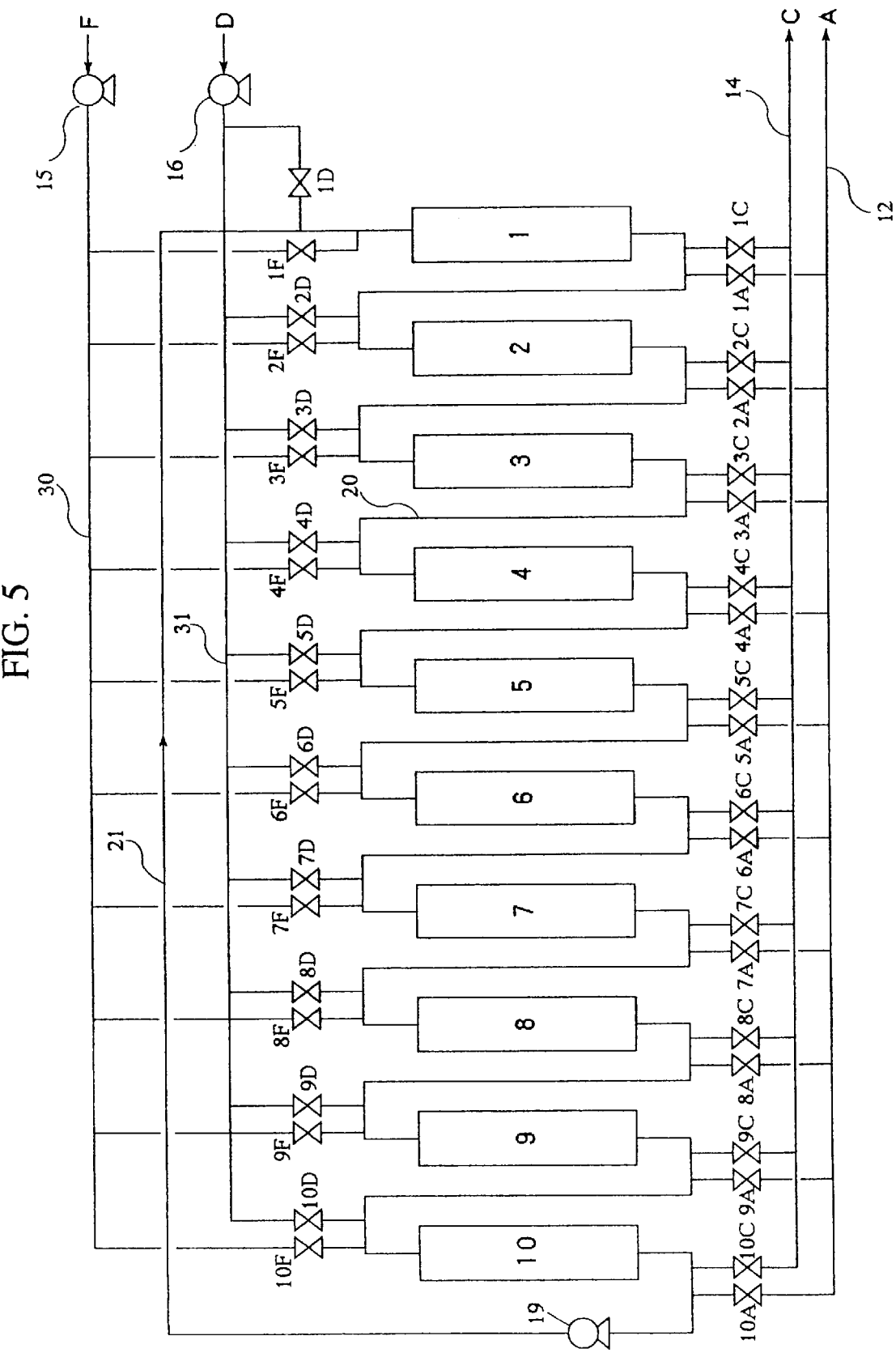
FIG. 5 is a schematic illustration of an example of the constitution of a simulated moving bed chromatographic separator that can be used for carrying out the process of the present invention for recovering betaine.

The following Examples will specifically illustrate the present invention, but should not be construed as limiting the scope of the present invention. FIG. 5 is a schematic illustration of an example of the constitution of a simulated moving bed chromatographic separator that can be used for carrying out the process of the present invention. The separator of FIG. 5 was used in Examples 1 and 2 and Comparative Example 1. In FIG. 5, numerals 1 to 10 refer to packing bed units (columns), 1A to 10A to raffinate withdrawal valves, 1C to 10C to extract withdrawal valves, 1D to 10D to eluent water feed valves, 1F to 10F to starting solution feed valves, A to raffinate (nonbetaine fraction solution), C to extract (betaine fraction solution), D to eluent water, F to starting solution (a starting solution material in Step 1, or a concentrate of crude betaine solution in Step 2 in Examples of the present invention), 12 to a raffinate withdrawal piping, 14 to an extract withdrawal piping, 15 to a starting solution feed pump, 16 to an eluent water feed pump, 19 to a circulating pump, 20 and 21 to connecting pipings, 30 to a starting solution feed piping, and 31 to an eluent water feed piping.

The ends of the packing bed units 1 to 10 each having an inner diameter of 108 mm and a height of 1.6 m are endlessly linked with the tops of the respective next packing bed units by means of the connecting pipings 20 and 21. The raffinate withdrawal valves 1A to 10A and the extract withdrawal valves 1C to 10C are connected to the connecting pipings on the downstream sides of the respective packing bed units, while connecting the connecting pipings with branch pipes having the respective starting solution feed valves 1F to 10F and branched from the starting solution feed piping 30 for the starting solution being fed by the starting solution feed pump 15, and with branch pipes having the respective eluent water feed valves 1D to 10D and branched from the eluent water feed piping 31 for eluent water being fed by the eluent water feed pump 16 on the upstream sides of the respective packing bed units. The circulating pump 19 is connected to the middle of the piping 21 extended from the end of the packing bed unit 10 to the top of the packing bed unit 1. The raffinate withdrawal valves 1A to 10A are connected to the raffinate withdrawal piping 12, while the extract withdrawal valves 1C to 10C are connected to the extract withdrawal piping 14.

The packing bed units were packed with a gel type strongly acidic cation exchange resin Amberlite CR-1320 manufactured by Rohm and Haas Company.

A generic description will now be made of the running operations of the simulated moving bed chromatographic separator of FIG. 5 used in Examples 1 and 2 and Comparative Example 1. In Stage 1, the starting solution feed valve 6F is opened to feed the starting solution via the top of the packing bed unit 6 and the eluent water feed valve 1D is opened to feed eluent water via the top of the packing bed unit 1 with internal liquid introduction from the end of the packing bed unit 10 into the top of the packing bed unit 1 via the circulating pump 19, while at the same time the extract withdrawal valve 2C is opened to withdraw extract containing a large amount of betaine from the end of the packing bed unit 2 and the raffinate withdrawal valve 8A is opened to withdraw raffinate containing a large amount of nonbetaine compounds such as salts from the end of the packing bed unit 8.

Accordingly, in this Stage 1, a first section ranging from the eluent water feed inlet to the extract withdrawal outlet involves 2 packing bed units, a second section ranging from the extract withdrawal outlet to the starting solution feed inlet involves 3 packing bed units, a third section ranging from the starting solution feed inlet to the raffinate withdrawal outlet involves 3 packing bed units, and a fourth section ranging from the raffinate withdrawal outlet to the eluent water feed inlet involves 2 packing bed units. Needless to say, however, the present invention is not limited to this embodiment.

In Stage 2 after the lapse of predetermined time, the eluent water feed valve 1D opened in Stage 1 is closed and the eluent water feed valve 2D is instead opened, while the opened extract withdrawal valve is displaced from 2C to 3C, the opened starting solution feed valve from 6F to 7F, and the opened raffinate withdrawal valve from 8A to 9A in the same manner as described just above.

Stages 3 to 10 of chromatographic separation are performed according to the foregoing operation of sequentially displacing every one of the opened valves one by one every stage on the downstream side in the direction of circulating flow. Generally speaking, such switching of valves results in performing an operation which apparently looks as if it moved the chromatographic packing in the direction opposite to that of circulating flow, and all stages are usually repeated continuously through a plurality of cycles as needed.

Incidentally, in the following Examples and Comparative Example, the solids-based composition is expressed in terms of areal percentage in high-performance liquid chromatography using a sodium-form ion exchange column and a differential refractometer, the term "one cycle time" denotes the time required for completing all stages ranging from Stage 1 to Stage 10, and the symbol "L" stands for liter(s).

Example 1

The solids content of a starting solution material (derived from sugar beet molasses) was 50 wt. % (615 g/L when converted in terms of volume-based concentration) as measured by a sugar refractometer, and the solids-based composition thereof was as follows:

| | |
|---|---|
| Salts | 66.3% |
| Trisaccharides | 4.7% |
| Disaccharides (sucrose and other disaccharides) | 9.1% |
| Monosaccharides | 3.0% |
| Betaine | 15.5% |
| Unknown Substances | 1.4% |

Monosaccharides included glucose, fructose, inositol, glycerol, etc., while the amount of salts per liter of the starting solution material was 2.9 eq/L in terms of the total cations content.

This starting solution material was fed as the starting solution to the simulated moving bed chromatographic separator to perform a demineralization operation in Step 1. In order to secure a high salts removal, a high betaine recovery and a large starting solution material throughput, operating conditions were set to be as follows:

Chromatographic Packing: 147 L of Amberlite CR-1320 (gel type strongly acidic cation exchange resin in monovalent ion form for chromatographic separation)

Operating Temperature: 80° C.

Linear Flow Velocity of Circulating Liquid between Starting Solution Inlet and Extract Withdrawal Outlet: 7.00 m/hr.

One Cycle Time: 68 min.

Feed Rate of Starting Solution: 14.7 L/hr. (0.10 L/L-packing/hr., based on packing)

Feed Rate of Eluent Water: 32.3 L/hr.

Withdrawal Rate of Extract: 22.0 L/hr.

Withdrawal Rate of Raffinate: 25. 0 L/hr.

Eluent Water/Starting Solution (vol. ratio): 2.2

As a result of operation, there were obtained extract and raffinate having the following respective solids contents and solids-based compositions:

|  | Extract | Raffinate |
|---|---|---|
| Solids Content | 91 g/L | 284 g/L |
| Salts | 0.1% | 85.3% |
| Trisaccharides | 0.4% | 6.0% |
| Disaccharides | 13.4% | 7.9% |
| Monosaccharides | 12.6% | 0.2% |
| Betaine | 68.4% | 0.3% |
| Unknown Substances | 5.1% | 0.3% |

Incidentally, the monovalent ion form of the gel type strongly acidic cation exchange resin packed in the columns was the Na form at the beginning of operation, but the ionic form composition thereof was composed of 26% of the Na form, 73% of the K form and 1% of the Ca form after the completion of operation.

The betaine recovery of the extract and the salts recovery of the raffinate (yardstick of salts removal when viewed from extract) as evaluated by the aforementioned high-performance liquid chromatography were 98.3% and 99.8%, respectively, based on the starting solution material.

In order to perform an operation in Step 2, a 1 N aqueous solution of calcium chloride, the amount of which was 30 L per packing bed unit, was flowed down through the 6 packing bed units 1, 2, 4, 6, 7 and 9 to change the ionic form of the cation exchange resin in those packing bed units to the Ca form. The extract obtained in Step 1 was concentrated to a saccharides content of 60 wt. % (772 g/L when converted in terms of volume-based concentration) as measured by the sugar refractometer. The resulting concentrate was subjected as the starting solution to chromatographic separation in Step 2 under the following operating conditions:

Operating Temperature: 80° C.

Linear Flow Velocity of Circulating Liquid between Starting

Solution Inlet and Extract Withdrawal Outlet: 7.00 m/hr.

One Cycle Time: 116 min.

Feed Rate of Starting Solution: 5.9 L/hr. (0.04 L/L-packing/hr., based on packing)

Feed Rate of Eluent Water: 44.8 L/hr.

Withdrawal Rate of Extract: 12.8 L/hr.

Withdrawal Rate of Raffinate: 37.9 L/hr.

Eluent Water/Starting Solution (vol. ratio): 7.6

As a result of operation, there were obtained extract and raffinate having the following respective solids contents and solids-based compositions:

|  | Extract | Raffinate |
|---|---|---|
| Solids Content | 232 g/L | 41 g/L |
| Salts | 0.0% | 0.2% |
| Trisaccharides | 0.0% | 1.0% |

-continued

|  | Extract | Raffinate |
|---|---|---|
| Disaccharides | 0.0% | 39.2% |
| Monosaccharides | 0.0% | 37.2% |
| Betaine | 97.2% | 12.7% |
| Unknown Substances | 2.8% | 9.7% |

Thus, extract having a betaine purity of 97.2% was obtained. Incidentally, the betaine recovery of the extract was 93.5%.

Example 2

A 1 N aqueous solution of calcium chloride, the amount of which was 30 L per packing bed unit, was flowed down through all the 10 packing bed units of the simulated moving bed chromatographic separator to change the ionic form of the cation exchange resin to the Ca form. The extract obtained in Step 1 in Example 1 was concentrated to a saccharides content of 60 wt. % (772 g/L when converted in terms of volume-based concentration) as measured by a sugar refractometer. The resulting concentrate was subjected as the starting solution to chromatographic separation in Step 2 under the following operating conditions:

Operating Temperature: 80° C.

Linear Flow Velocity of Circulating Liquid between Starting Solution Inlet and Extract Withdrawal Outlet: 7.00 m/hr.

One Cycle Time: 133 min.

Feed Rate of Starting Solution: 7.4 L/hr. (0.050 L/L-packing/hr., based on packing)

Feed Rate of Eluent Water: 50.0 L/hr.

Withdrawal Rate of Extract: 14.0 L/hr.

Withdrawal Rate of Raffinate: 43. 4 L/hr.

Eluent Water/Starting Solution (vol. ratio): 6.8

As a result of operation, there were obtained extract and raffinate having the following respective solids contents and solids-based compositions:

|  | Extract | Raffinate |
|---|---|---|
| Solids Content | 265 g/L | 46 g/L |
| Salts | 0.0% | 0.2% |
| Trisaccharides | 0.0% | 1.0% |
| Disaccharides | 0.0% | 38.6% |
| Monosaccharides | 0.0% | 36.6% |
| Betaine | 99.7% | 9.2% |
| Unknown Substances | 0.3% | 14.4% |

Incidentally, the betaine recovery of the extract was 95.3%. A change in all the ionic form (based on ion exchange capacity) of the cation exchange resin to the Ca form could increase the starting solution throughput by 25% in comparison with that in Example 1 with a decrease in the amount of unknown substances mixed in the extract, whereby the betaine solution (extract) having so high a betaine purity of 99.7% could be recovered.

Comparative Example 1

The same starting solution material as used in Step 1 in Example 1 was fed as the starting solution to the simulated moving bed chromatographic separator. In order to obtain high-purity betaine only in Step 1, operating conditions were set to be as follows:

Chromatographic Packing: 147 L of Amberlite CR-1320 (gel type strongly acidic cation exchange resin in monovalent ion form for chromatographic separation)

Operating Temperature: 80° C.

Linear Flow Velocity of Circulating Liquid between Starting Solution Inlet and Extract Withdrawal Outlet: 7.00 m/hr.

One Cycle Time: 79 min.

Feed Rate of Starting Solution: 5.9 L/hr. (0.04 L/L-packing/hr., based on packing)

Feed Rate of Eluent Water: 30.4 L/hr.

Withdrawal Rate of Extract: 7.6 L/hr.

Withdrawal Rate of Raffinate: 28.7 L/hr.

Eluent Water/Starting Solution (vol. ratio): 5.2

Incidentally, the monovalent ion form of the gel type strongly acidic cation exchange resin packed in the columns was the Na form at the beginning of operation, but the ionic form composition thereof was composed of 26% of the Na form, 73% of the K form and 1% of the Ca form after the completion of operation.

As a result of operation, there were obtained extract and raffinate having the following respective solids contents and solids-based compositions:

|  | Extract | Raffinate |
| --- | --- | --- |
| Solids Content | 81 g/L | 106 g/L |
| Salts | 0.1% | 80.0% |
| Trisaccharides | 0.0% | 5.7% |
| Disaccharides | 0.7% | 10.9% |
| Monosaccharides | 13.0% | 0.9% |
| Betaine | 81.9% | 1.7% |
| Unknown Substances | 4.3% | 0.8% |

The betaine recovery of the extract and the salts recovery of the raffinate were 90.6% and 99.8%, respectively. Although an attempt to heighten the betaine purity was made by decreasing the load (feed rate) of the starting solution material and lowering the betaine recovery in comparison with those in Step 1 in Example 1, the betaine purity was only 81.9% with a failure in separating betaine from monosaccharides and unknown substances.

INDUSTRIAL APPLICABILITY

According to the present invention, there can be provided a technology capable of obtaining a high-quality betaine solution having a betaine purity of at least 90 wt. % with industrial-scale equipment.

What is claimed is:

1. A process for recovering betaine from a starting solution material in the form of a) waste produced in the course of separation and recovery of sucrose from sugar beet extract or sugar beet molasses with a 2-component separation simulated moving bed chromatographic separator using a strongly acidic cation exchange resin in a salt form as chromatographic packing or b) a concentrate of said waste; said process comprising Step 1 of separating a demineralized crude betaine fraction from said starting solution material with a 2-component separation simulated moving bed chromatographic separator using as chromatographic packing a strongly acid cation exchange resin in an ionic form equilibrated with ions of said starting solution material, and Step 2 of separating and recovering a betaine fraction from said crude betaine fraction or its concentrate with a 2-component separation simulated moving bed chromatographic separator using as chromatographic packing a strongly acidic cation exchange resin having at least 10% (based on the ion exchange capacity) of the ionic form thereof changed to the Ca form.

2. A process for recovering betaine as claimed in claim 1, wherein said Step 1 and said Step 2 are preformed using the same 2-component separation simulated moving bed chromatographic separator.

3. A process for recovering betaine as claimed in claim 2, wherein said Step 1 and said Step 2 are preformed in separate seasons, and wherein at least 95% (based on ion exchange capacity) of the ionic form of said strongly acidic cation exchange resin is changed to a monovalent alkali ion form before start of said Step 1 and at least 10% (based on ion exchange capacity) of the ionic form of said strongly acidic cation exchange resin is changed to the Ca form before start of said Step 2.

4. A process for recovering betaine as claimed in claim 3, wherein a concentrate of said crude betaine fraction obtained in said Step 1 is stored until said Step 2 is preformed.

\* \* \* \* \*